United States Patent
Paul et al.

(10) Patent No.: US 9,133,188 B2
(45) Date of Patent: Sep. 15, 2015

(54) METHODS FOR PREPARING NAPHTHYRIDINES

(75) Inventors: Dharam Paul, Flinders Park (AU); Andrew John Harvey, Goodwood (AU); Bernard Luke Flynn, Donvale (AU)

(73) Assignee: Bionomics Limited, Thebarton (AU)

( * ) Notice: Subject to any disclaimer, the term of this patent is extended or adjusted under 35 U.S.C. 154(b) by 0 days.

(21) Appl. No.: 14/116,196

(22) PCT Filed: May 11, 2012

(86) PCT No.: PCT/AU2012/000533
§ 371 (c)(1),
(2), (4) Date: Jan. 15, 2014

(87) PCT Pub. No.: WO2012/151640
PCT Pub. Date: Nov. 15, 2012

(65) Prior Publication Data
US 2014/0128600 A1    May 8, 2014

(30) Foreign Application Priority Data
May 12, 2011    (AU) .................... 2011901791

(51) Int. Cl.
C07D 471/04    (2006.01)
A61K 31/4375    (2006.01)
C07D 213/76    (2006.01)

(52) U.S. Cl.
CPC .......... *C07D 471/04* (2013.01); *A61K 31/4375* (2013.01); *C07D 213/76* (2013.01)

(58) Field of Classification Search
CPC ................................... C07D 471/04
USPC ...................................... 546/123
See application file for complete search history.

(56) References Cited

U.S. PATENT DOCUMENTS

| | | |
|---|---|---|
| 3,429,887 A | 2/1969 | Lesher et al. |
| 4,226,864 A | 10/1980 | Narisada et al. |
| 4,404,201 A | 9/1983 | Haskell et al. |
| 5,095,015 A | 3/1992 | Albaugh |
| 5,182,290 A | 1/1993 | Albaugh |
| 5,182,386 A | 1/1993 | Albaugh et al. |
| 5,212,310 A | 5/1993 | Thurkauf et al. |
| 5,306,819 A | 4/1994 | Albaugh et al. |
| 5,312,822 A | 5/1994 | Albaugh |
| 5,328,912 A | 7/1994 | Albaugh |
| 5,451,585 A | 9/1995 | Albaugh |
| 5,473,073 A | 12/1995 | Albaugh et al. |
| 5,484,944 A | 1/1996 | Albaugh et al. |
| 5,510,480 A | 4/1996 | Albaugh |
| 5,608,079 A | 3/1997 | Albaugh et al. |
| 5,625,063 A | 4/1997 | Thurkauf et al. |
| 5,723,462 A | 3/1998 | Albaugh et al. |
| 5,750,702 A | 5/1998 | Albaugh et al. |
| 5,804,686 A | 9/1998 | Albaugh et al. |
| 5,817,813 A | 10/1998 | Thurkauf et al. |
| 5,925,770 A | 7/1999 | Albaugh et al. |
| 6,013,650 A | 1/2000 | Thurkauf et al. |
| 6,080,873 A | 6/2000 | Albaugh et al. |
| 6,096,887 A | 8/2000 | Albaugh et al. |
| 6,143,760 A | 11/2000 | Albaugh et al. |
| 6,166,203 A | 12/2000 | Cai et al. |
| 6,177,569 B1 | 1/2001 | Rachwal et al. |
| 6,211,365 B1 | 4/2001 | Albaugh et al. |
| 6,229,017 B1 | 5/2001 | Lui et al. |
| 6,297,256 B1 | 10/2001 | Cai et al. |
| 6,353,109 B1 | 3/2002 | Albaugh et al. |
| 6,399,604 B1 | 6/2002 | Albaugh et al. |
| 6,413,956 B1 | 7/2002 | Albaugh et al. |
| 6,414,147 B1 | 7/2002 | Currie et al. |
| 6,423,711 B1 | 7/2002 | Cai et al. |
| 6,423,956 B1 | 7/2002 | Mandella et al. |
| 6,511,987 B1 | 1/2003 | Yuan et al. |
| 6,515,140 B2 | 2/2003 | Albaugh et al. |
| 6,559,163 B2 | 5/2003 | Cai et al. |
| 6,646,124 B2 | 11/2003 | Albaugh et al. |

(Continued)

FOREIGN PATENT DOCUMENTS

| | | |
|---|---|---|
| AU | 2005204365 A1 | 7/2005 |
| AU | 2005209365 A1 | 8/2005 |

(Continued)

OTHER PUBLICATIONS

International Search Report and Written Opinion for PCT/AU2007/001566 mailed Nov. 20, 2007.
International Preliminary Report on Patentability for PCT/AU2007/001566, completed Oct. 1, 2008.
International Search Report and Written Opinion for PCT/AU2012/000223 mailed Apr. 4, 2012.
International Preliminary Report on Patentability for PCT/AU2012/000223, mailed Sep. 12, 2013.
International Search Report and Written Opinion for PCT/AU2012/000216 mailed Mar. 15, 2012.
International Preliminary Report on Patentability for PCT/AU2012/000216, mailed Sep. 12, 2013.

(Continued)

*Primary Examiner* — Niloofar Rahmani
(74) *Attorney, Agent, or Firm* — Wolf, Greenfield & Sacks, P.C.

(57) ABSTRACT

The present invention provides methods of synthesizing compounds of formula (1) and intermediates thereto. The present invention also provides intermediates useful in the synthesis of compounds of formula (1).

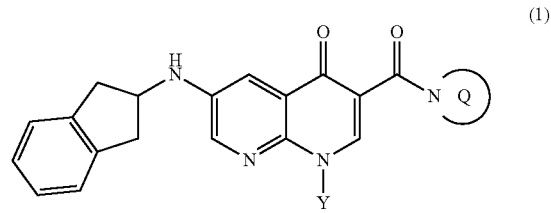

(1)

19 Claims, No Drawings

(56) References Cited

U.S. PATENT DOCUMENTS

| | | | |
|---|---|---|---|
| 6,656,941 B2 | 12/2003 | Maynard et al. | |
| 6,703,393 B2 | 3/2004 | Li et al. | |
| 6,720,339 B2 | 4/2004 | Albaugh et al. | |
| 6,723,332 B2 | 4/2004 | Cai et al. | |
| 6,828,329 B2 | 12/2004 | Cai et al. | |
| 7,829,694 B2 | 11/2010 | Kaemmerer | |
| 8,293,737 B2* | 10/2012 | Baell et al. | 514/234.5 |
| 8,551,990 B2* | 10/2013 | Baell et al. | 514/234.5 |
| 8,614,212 B2* | 12/2013 | Baell et al. | 514/234.5 |
| 8,906,912 B2 | 12/2014 | Baell et al. | |
| 2002/0151591 A1 | 10/2002 | Villalobos et al. | |
| 2004/0082555 A1 | 4/2004 | Villalobos | |
| 2005/0009861 A1 | 1/2005 | Villalobos et al. | |
| 2005/0182085 A1 | 8/2005 | Defossa et al. | |
| 2005/0182086 A1 | 8/2005 | Defossa et al. | |
| 2005/0182087 A1 | 8/2005 | Defossa et al. | |
| 2010/0105678 A1 | 4/2010 | Baell et al. | |
| 2014/0045839 A1 | 2/2014 | Baell et al. | |
| 2014/0051701 A1* | 2/2014 | O'Connor et al. | 514/234.5 |
| 2014/0088104 A1 | 3/2014 | Flynn et al. | |

FOREIGN PATENT DOCUMENTS

| | | |
|---|---|---|
| AU | 2005209367 A1 | 8/2005 |
| AU | 2005209368 A1 | 8/2005 |
| CA | 1114822 A | 12/1981 |
| EP | 0 341 990 A2 | 11/1989 |
| EP | 0 531 958 A1 | 3/1999 |
| JP | 50-023036 B | 8/1975 |
| JP | 50-023037 B | 8/1975 |
| JP | 51-032594 A | 3/1976 |
| JP | 55-111486 A | 8/1980 |
| JP | 55-151584 A | 11/1980 |
| JP | 56-115787 A | 9/1981 |
| JP | 56-118081 A | 9/1981 |
| JP | 56-118083 A | 9/1981 |
| JP | 57-026688 A | 2/1982 |
| JP | 57-109790 A | 7/1982 |
| JP | 59-093080 A | 5/1984 |
| JP | 2002-544197 A | 12/2004 |
| JP | 2005-162726 A | 6/2005 |
| JP | 2006-508989 A | 3/2006 |
| WO | WO 00/68202 A1 | 11/2000 |
| WO | WO 02/060872 A1 | 8/2002 |
| WO | WO 02/069948 A1 | 9/2002 |
| WO | WO 03/045313 A2 | 6/2003 |
| WO | WO 03/045920 A1 | 6/2003 |
| WO | WO 03/097564 A2 | 11/2003 |
| WO | WO 2004/048374 A1 | 6/2004 |
| WO | WO 2004/058144 A2 | 7/2004 |
| WO | WO 2004/064721 A2 | 8/2004 |
| WO | WO 2004/083207 A1 | 9/2004 |
| WO | WO 2005/073229 A1 | 8/2005 |
| WO | WO 2005/073230 A1 | 8/2005 |
| WO | WO 2005/073231 A1 | 8/2005 |
| WO | WO 2005/097750 A1 | 10/2005 |
| WO | WO 2006/048146 A2 | 5/2006 |
| WO | WO 2006/060390 A1 | 6/2006 |
| WO | WO 2006/128802 A2 | 12/2006 |
| WO | WO 2007/039172 A1 | 4/2007 |
| WO | WO 2008/021210 A2 | 2/2008 |
| WO | WO 2008/046135 A1 | 4/2008 |
| WO | WO 2010/135360 A1 | 11/2010 |
| WO | WO 2012/116410 A1 | 9/2012 |
| WO | WO 2012/116415 A1 | 9/2012 |
| WO | WO 2012/151640 A1 | 11/2012 |

OTHER PUBLICATIONS

International Search Report and Written Opinion for PCT/AU2012/000533 mailed May 31, 2012.

International Preliminary Report on Patentability for PCT/AU2012/000533, mailed Nov. 21, 2013.

International Search Report and Written Opinion for PCT/AU2013/000991, mailed Oct. 11, 2013.

[No Author Listed] Mayo Clinc, "Anxiety." Available at http://www.mayoclinic.com/health/anxiety/DS01187. Last accessed Jan. 4, 2012.

[No Author Listed] Medline Plus, "Autoimmune disorders," National Institutes of Health. Available at http://www.nlm.nih.gov/medlineplus/ency/article/000816.html. Last accessed Jun. 3, 2011.

Abdel-Magid et al., Reductive Amination of Aldehydes and Ketones with Sodium Triacetoxyborohydride. Studies on Direct and Indirect Reductive Amination Procedures(1). J Org Chem. May 31, 1996 ;61(11) :3849-3862.

Berge et al., Pharmaceutical salts. J Pharm Sci. Jan. 1977;66(1):1-19.

Castagné et al., Early behavioral screening for antidepressants and anxiolytics. Drug Dev Res. 2006;67(9):729-742.

Chopin et al., The benzodiazepine antagonist flumazenil blocks the effects of CCK receptor agonists and antagonists in the elevated plus-maze. Psychopharmacology (Berl). 1993;110(4):409-14.

Chung et al., Trimethylaluminium-Facilitated Direct Amidation of Carboxylic Acids. Synlett. 2011;14:2072-2074.

Collini et al., The solid phase synthesis of tri-substituted indoles. Tetrahedron Lett. 1997;38(46): 7963-66.

Cryan et al., The age of anxiety: role of animal models of anxiolytic action in drug discovery. Br J Pharmacol. Oct. 2011;164(4):1129-61. doi: 10.1111/j.1476-5381.2011.01362.x.

Fassold et al., A new assay for nerve fiber repulsion. Ann N Y Acad Sci. Apr. 2010;1193:43-7. doi: 10.1111/j.1749-6632.2009.05295.x.

Flynn et al., A novel palladium-mediated coupling approach to 2,3-disubstituted benzo(b)thiophenes and its application to the synthesis of tubulin binding agents. Org Lett. Mar. 8, 2001;3(5):651-4.

Gezginci et al., Antimycobacterial activity of substituted isosteres of pyridine- and pyrazinecarboxylic acids. 2. J Med Chem. May 10, 2001;44(10):1560-3.

Han et al., Solid phase parallel synthesis of highly substituted thiophene derivatives and identification of novel phosphodiesterase-4 (PDE-4) inhibitors. Tetrahedron. 1999;55(39):11669-85.

Heindl et al., Studies on the antibacterial activity of quinolone carboxylic acids. IX. Aza analogs. Di- and trisubstituted 1,4-dihydro-4-oxo-1, 5-naphthyridine-3 carboxylic acids and 1-ethyl-4-pyridone-3 carboxylic acids. European Journal of Medicinal Chemistry. 1977;12(6):549-55. German.

Heinrichs et al., Brain penetrance, receptor occupancy and antistress in vivo efficacy of a small molecule corticotropin releasing factor type I receptor selective antagonist. Neuropsychopharmacology. Aug. 2002;27(2):194-202.

Johnson et al., Solid phase chemistry approach to the SAR development of a novel class of active site-directed thrombin inhibitors. Tetrahedron. 1999;55:11641-52.

Kaffy et al., Synthesis and biological evaluation of vinylogous combretastatin A-4 derivatives. Org Biomol Chem. Jul. 21, 2005;3(14):2657-60. Epub Jun. 21, 2005.

Maslankiewicz et al., Synthesis and Amination of 4-Chloro-3-quinolinesulfonyl Chloride. Heterocycles. 1994;38(6):1317-31.

Maslankiewicz, From Haloquinolines and Halopyridines to Quinoline- and Pyridinesulfonyl Chlorides and Sulfonamides. Heterocycles. 2007;71(9):1975-90.

Nishimura et al., Conformational analysis of tandospirone in aqueous solution: lead evolution of potent dopamine D4 receptor ligands. Bioorg Med Chem Lett. May 7, 2001;11(9):1141-4.

Pettit et al., Antineoplastic agents 322. Synthesis of combretastatin A-4 prodrugs. Anticancer Drug Des. Jun. 1995;10(4):299-309.

Porsolt et al., Behavioural despair in rats: a new model sensitive to antidepressant treatments. Eur J Pharmacol. Feb. 15, 1978;47(4):379-91.

(56) References Cited

OTHER PUBLICATIONS

Soskic et al., QSAR study of 1,8-naphthyridin-4-ones as inhibitors of photosystem II. J Chem Inf Comput Sci. Sep.-Oct. 2001;41(5):1316-21.

Temple et al., Synthesis of potential antimalarial agents. VIII. Azaquinolines. II. Preparation of some 1,5-Naphthyridines and pyrido[3,2-d]pyrimidines. J Heterocyclic Chem. 1970;7(5):1219-22. Abstract Only.

Vercek et al., Heterocycles. 182. Neighboring group interaction in ortho-substituted heterocycles. 2. 1,2,4-Oxadiazolylpyridines and pyrido[2,3-d]pyrimidine 3-oxides. J Org Chem. 1979;44(10):1695-1699.

* cited by examiner

METHODS FOR PREPARING NAPHTHYRIDINES

RELATED APPLICATION

This application is a national stage filing under 35 U.S.C. §371 of international PCT application, PCT/AU2012/000533, filed May 11, 2012, which claims the benefit of Australian Patent Application No. 2011901791, filed May 12, 2011, each of which is hereby incorporated by reference in its entirety.

FIELD OF THE INVENTION

The present invention relates to the synthesis of substituted 1,8-naphthyridine compounds.

BACKGROUND OF THE INVENTION

WO 2008/046136 (PCT/AU2007/001566) discloses, inter alia, substituted 1,8-naphthyridine compounds of the following general class:

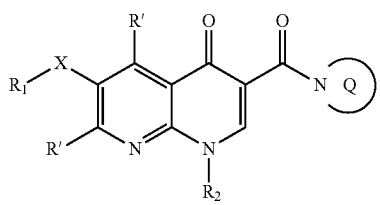

These compounds have been shown to possess anxiolytic activity without sedative side-effects and therefore represent an attractive pharmacological alternative to the 1,4-benzodiazepine class of anxiolytics such as diazepam (commonly known as Valium®).

While the synthesis of the 1,8-naphthyridines has been quite successful on a laboratory scale (that is, mg scale) the use of this methodology to produce larger amounts (e.g., kilogram scale) of a particular class of 1,8-naphthyridines has proven to be challenging. This has caused the present inventors to devise new scale up methodology to overcome the current deficiencies which exist in the art. The present invention is directed to addressing these shortcomings to enable the synthesis of 1,8-naphthyridines on a larger scale.

SUMMARY OF THE INVENTION

In one aspect, the present invention provides methods of preparing compounds of formula (1)

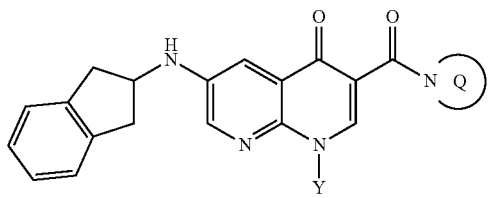

wherein Q is an optionally substituted N-containing heterocyclyl or optionally substituted N-containing heteroaryl, and Y is a lower alkyl group;

comprising:

a) treating a compound of formula (2)

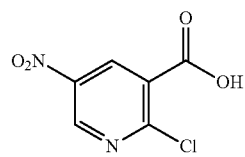

with an acid activating agent, a non-nucleophilic base, lower alkyl N,N-lower dialkyl aminoacrylate and lower alkylamine, under conditions sufficient to obtain a compound of formula (3)

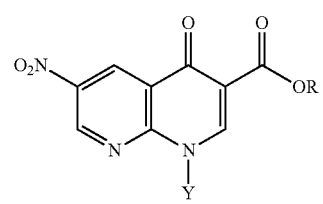

wherein R is lower alkyl, b) reducing the nitro group of the compound of formula (3) from step (a) to obtain a compound of formula (4)

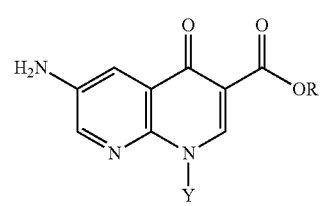

c) treating the compound of formula (4) from step (b) with 2-indanone and a suitable reducing agent under conditions sufficient to obtain a compound of formula (5)

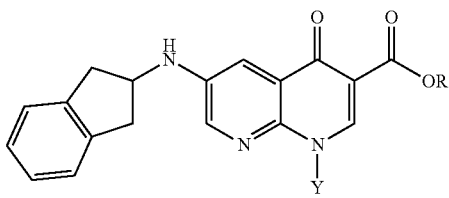

d) hydrolysing the compound of formula (5) from step (c) to obtain a compound of formula (6); and

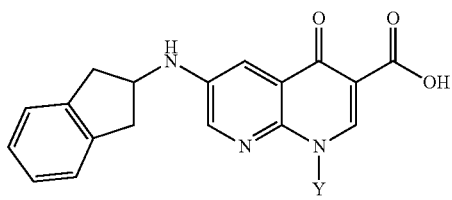

(6)

e) reacting (6) with an acid activating agent and QH, under conditions sufficient to obtain a compound of formula (1).

In another aspect, the present invention provides methods for preparing a compound of formula (3)

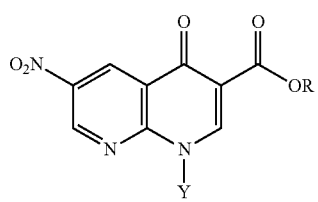

(3)

wherein Y and R are independently lower alkyl; comprising:
a) reacting a compound of formula (2)

(2)

with a chlorinating agent under conditions sufficient to obtain a compound of formula (2a)

(2a)

b) treating the compound of formula (2a) from step a) with a non-nucleophilic base and lower alkyl N,N-lower dialkyl aminoacrylate to obtain a compound of formula (2b)

(2b)

wherein R and R' are independently lower alkyl; and c) reacting the compound of formula (2b) from step (b) with a lower alkylamine under conditions sufficient to form (3).

In still another aspect, the present invention provides compounds of formula (2b) and salts thereof:

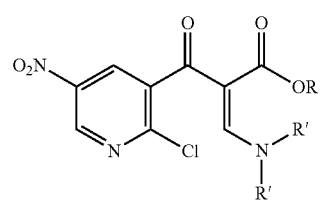

(2b)

wherein R and R' are independently lower alkyl.

In yet another aspect, the present invention provides a compound of formula (2c) and salts thereof:

(2c)

In another aspect, the present invention provides methods for preparing a compound of formula (1)

(1)

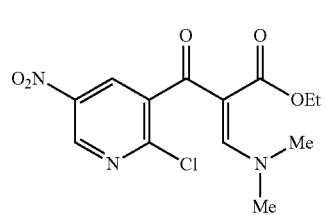

wherein Q is an optionally substituted N-containing heterocyclyl or optionally substituted N-containing heteroaryl and Y is a lower alkyl group;
comprising:
a) reacting a compound of formula (6)

(6)

with an acid activating agent in the presence of non-nucleophilic base in a suitable solvent and reacting the resultant product with QH under conditions sufficient to obtain a compound of formula (1); and
b) purifying the compound of formula (1) obtained from step a) by washing with a weakly basic solution.

DETAILED DESCRIPTION OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The present invention is based on the discovery that compounds of formula (1), as described herein can be prepared efficiently and in good to high yields in kilogram-scale quantities by utilising newly advanced methodology which is shown herein to be amenable to large scale production of chemical compounds in terms of chemical efficiency and reagent safety.

The term "alkyl" as used alone or in combination herein refers to a straight or branched chain saturated hydrocarbon group. The term "lower alkyl" refers to such groups containing from one to six carbon atoms, such as methyl ("Me"), ethyl ("Et"), n-propyl, isopropyl, n-butyl, isobutyl, sec-butyl, tert-butyl and the like.

The term "alkynyl" refers to a linear or branched monovalent hydrocarbon radical with at least one site of unsaturation, i.e., a carbon-carbon sp triple bond, preferably having from 2 to 10 carbon atoms and more particularly 2 to 6 carbon atoms and having at least 1, and particularly from 1-2, carbon to carbon, triple bonds. Examples of alkynyl groups include ethynyl (—C≡CH), propargyl (—CH$_2$C≡CH), pent-2-ynyl (—CH$_2$C≡CCH$_2$—CH$_3$), and the like.

The term "alkenyl" refers to a monovalent hydrocarbon radical with at least one site of unsaturation, i.e., a carbon-carbon, sp$^2$ double bond, which may be straight chained or branched and particularly have from 2 to 10 carbon atoms and more particularly 2 to 6 carbon atoms and have at least 1 and particularly from 1-2, carbon to carbon, double bonds. An alkenyl radical includes radicals having "cis" and "trans" orientations, or alternatively, "E" and "Z" orientations. Examples include ethenyl (—CH=CH$_2$), n-propenyl (—CH$_2$CH=CH$_2$), iso-propenyl (—C(CH$_3$)=CH$_2$), but-2-enyl (—CH$_2$CH=CHCH$_3$), and the like.

The term "cycloalkyl" refers to cyclic alkyl groups having a single cyclic ring or multiple condensed rings, preferably incorporating 3 to 11 carbon atoms. Such cycloalkyl groups include, by way of example, single ring structures such as cyclopropyl, cyclobutyl, cyclopentyl, cyclohexyl, cyclooctyl, and the like. The term also includes polycyclic ring systems where the cycloalkyl ring is fused with one or more aromatic or non-aromatic carbocyclic or heterocyclic rings, such as adamantanyl, indanyl, 1,2,3,4-tetrahydronapthalenyl and the like.

The term "lower alkylamine" refers to a "lower alkyl-NH$_2$" where lower alkyl is as defined above.

In some embodiments, Y is C$_{1-3}$ alkyl. In certain embodiments, Y is methyl or ethyl. In other embodiments, Y is ethyl.

The term "N-containing heteroaryl" refers to a monovalent aromatic heterocyclic group, preferably having from 2 to 10 carbon atoms, and 1 to 4 heteroatoms selected from nitrogen, oxygen, and sulfur within the ring, wherein at least one heteroatom is nitrogen. Such heteroaryl groups can have a single ring (e.g., pyridyl, pyrrolyl or imidazolyl) or multiple condensed rings (e.g., indolinyl or benzimidazolyl).

The term "N-containing heterocyclyl" refers to a monovalent saturated or unsaturated group having a single ring or multiple condensed rings, preferably from 1 to 8 carbon atoms, and from 1 to 4 heteroatoms selected from nitrogen, oxygen, and sulfur within the ring, wherein at least one heteroatom is nitrogen.

Examples of 5-membered monocyclic N-containing heterocyclyl and N-containing heteroaryl groups include pyrrolyl, H-pyrrolyl, pyrrolinyl, pyrrolidinyl, furazanyl, pyrazolyl, pyrazolinyl, pyrazolidinyl, imidazolyl, imidazolinyl, triazolyl (including 1,2,3 and 1,3,4 triazolyls) and tetrazolyl.

Examples of 6-membered monocyclic N-containing heterocyclyl and N-containing heteroaryl groups include pyridyl, piperidinyl, morpholinyl, thiomorpholinyl and piperazinyl.

The above heterocycles may be optionally substituted with a broad range of substituents, such as C$_{1-6}$ alkyl, C$_{1-6}$ alkoxy, C$_{2-6}$ alkenyl, C$_{2-6}$ alkynyl, halo, hydroxy, mercapto, C$_{1-6}$ haloalkyl, phenyl, phenyloxy, phenylalkyl, phenylalkyloxy, amino, cyano, or mono or di(C$_{1-6}$ alkyl)amino.

As referred to above the N-containing heterocycle or heteroaryl may be fused to a carbocyclic aromatic ring such as phenyl, naphthyl, indenyl, azulenyl, fluorenyl, and anthracenyl; or a heteroaryl ring such as pyridyl, pyrimidinyl, pyridazinyl, pyrazinyl, pyrrolyl, and imidazole.

Examples of 8, 9 and 10-membered bicyclic N-containing heterocyclyl and N-containing heteroaryl groups include 1H-thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, phthalazinyl, quinazolinyl, quinoxalinyl, benzotriazinyl, pteridinyl, pyrrolopyridine and the like. These heterocycles may be optionally substituted, for example, with C$_{1-6}$ alkyl, C$_{1-6}$ alkoxy, C$_{2-6}$ alkenyl, C$_{2-6}$ alkynyl, halo, hydroxy, mercapto, C$_{1-6}$ haloalkyl, cyano, phenyl, phenyloxy, phenylalkyl, phenylalkyloxy, amino, and mono or di(C$_{1-6}$ alkyl)amino.

Exemplary N-containing heterocyclic and N-containing heteroaromatic radicals for the Q group include (optionally substituted) piperazinyl, piperidinyl, pyrrolidinyl, azetidinyl, azepanyl, diazepanyl, morpholinyl, thiomorpholinyl, pyrrolyl, imidazolyl, pyrazolyl, indolyl, isoindolyl, 3H-indolyl, and indolinyl. These radicals can be optionally substituted with, by example, C$_{1-6}$ alkyl, C$_{1-6}$ alkoxy, C$_{2-6}$ alkenyl, C$_{2-6}$ alkynyl, halo, hydroxy, mercapto, C$_{1-6}$ haloalkyl, amino, phenyl, phenyloxy, phenylalkyl, phenylalkyloxy, cyano, or mono or di(C$_{1-6}$alkyl)amino.

In some embodiments, the N-containing heteroaryl or N-containing heteroaromatic ring group Q is piperazinyl, morpholinyl, piperidinyl, or pyrrolidinyl.

In certain embodiments, Q is morpholinyl.

As used herein, the term "optionally substituted" means that a group may include one or more substituents. One or more hydrogen atoms on the group may be replaced by substituent groups independently selected from halogen, C$_{1-6}$ alkyl, C$_{2-6}$ alkenyl, C$_{2-6}$ alkynyl, —(CH$_2$)$_p$—C$_{3-7}$ cycloalkyl, —(CH$_2$)$_p$—C$_{4-7}$ cycloalkenyl, —(CH$_2$)$_p$-aryl, —(CH$_2$)$_p$-heterocyclyl, —(CH$_2$)$_p$-heteroaryl, —C$_6$H$_4$S(O)$_q$—C$_{1-6}$ alkyl, —C(Ph)$_3$, —CN, —OR$^a$, —O(CH$_2$)$_{1-6}$—R$^a$, —O—(CH$_2$)$_{1-6}$—OR$^a$, —OC(O)R$^a$, —C(O)R$^a$, —C(O)OR$^a$, —OC(O)OR$^a$, —OC(O)NR$^b$R$^c$, —NR$^b$R$^c$, —NRC(O)R$^b$, —NRC(O)NR$^b$R$^c$, —NRC(S)NR$^b$R$^c$, —NRS(O)$_2$R$^b$, —NRC(O)OR$^b$, —C(NR)NR$^b$R$^c$, —C(=NOR$^b$)R$^a$, —C(=NOH)NR$^b$R$^c$, —C(O)NR$^b$R$^c$, —C(=NCN)—NR$^b$R$^c$, —C(=NR)NR$^b$R$^c$, —C(=NR$^b$)SR$^c$, —NR$^b$C(=NCN)SR$^c$, —CONR$^a$SO$_2$R$^b$, —C(S)NR$^b$R$^c$, —S(O)$_q$R$^a$, —SO$_2$NR$^b$R$^c$, —SO$_2$NR$^a$C(O)R$^b$, —OS(O)$_2$R$^a$, —PO(OR$^a$)$_2$, —NO$_2$, —CN, mercapto, where p is 0-6, q is 0-2, and each R$^a$, R$^b$ and R$^c$ is independently selected from H, C$_{1-6}$ alkyl, C$_{2-6}$ alkenyl, C$_{2-6}$ alkynyl, C$_{3-7}$ cycloalkyl, C$_{4-7}$ cycloalkenyl, aryl, heterocyclyl, heteroaryl, C$_{1-6}$ alkylaryl, C$_{1-6}$ alkylheteroaryl, and C$_{1-6}$ alkylheterocyclyl, wherein the alkyl, alkenyl, alkynyl, cycloalkyl, cycloalkenyl, aryl, heterocyclyl, heteroaryl, C$_{1-6}$ alkylaryl, $C_{1-6}$ alkylheteroaryl, or $C_{1-6}$ alkylheterocyclyl, may be optionally substituted with one to six of same or different groups selected from halogen, hydroxy, lower alkyl, lower alkoxy, —$CO_2H$, $CF_3$, CN, phenyl, $NH_2$ and —$NO_2$; or when $R^b$ and $R^c$ are attached to the same nitrogen atom, they may, together with the atom to which they are attached, form a 5- to 7-membered nitrogen containing heterocyclic ring.

In certain embodiments, Y is ethyl and Q is morpholinyl.

In certain embodiments, an inventive method comprises the formation of an acrylate ester of formula (2b) from the acid chloride (formula (2a)) of 2-chloro-5-nitro-nicotinic acid (formula (2)); and a subsequent cyclisation step (in situ) to form a 1,8-naphthyridine of formula (3). The preparation of a compound of formula (2) is detailed in WO 2008/046135. The substituted pyridine of formula (2) is commercially available from Shanghai FWD Chemicals Limited.

In a further aspect, the present invention provides methods of preparing a compound of formula (2b):

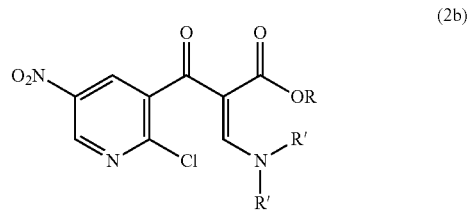
(2b)

wherein R and R' are independently lower alkyl;
comprising:
  a) treating a compound of formula (2)

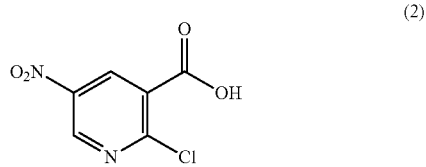 [SMILES: O=C(O)c1cc([N+](=O)[O-])cnc1Cl]
(2)

with a chlorinating agent, under conditions sufficient to obtain a compound of formula (2a)

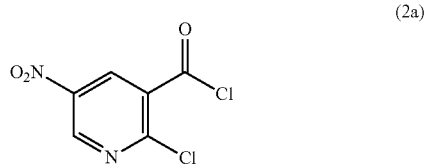 [SMILES: O=C(Cl)c1cc([N+](=O)[O-])cnc1Cl]
(2a)

b) treating the compound of formula (2a) from step a) with a non-nucleophilic base and lower alkyl N,N-lower dialkyl aminoacrylate to obtain a compound of formula (2b).

In some embodiments, the chlorinating agent is selected from thionyl chloride, oxalyl chloride, pivaloyl chloride, phosphorus pentachloride, and phosphorus oxychloride. In certain embodiments, the chlorinating agent is thionyl chloride.

In some embodiments, a compound of formula (2) is treated with 2 to 4 equivalents of thionyl chloride in a chlorinated solvent. In certain embodiments, the chlorinated solvent is chloroform. In certain embodiments, the reaction is conducted at reflux. In certain embodiments, the reaction is conducted in the presence of a catalytic amount of DMF (dimethyl formamide). In certain embodiments, between about 1-10% of DMF (relative to chloroform) is added, and in another embodiment about 2-5%, and in a further embodiment about 2.5% DMF.

In certain embodiments, a compound of formula (2) is treated with about 2 to 4 equivalents of thionyl chloride in chloroform at reflux wherein the chloroform comprises about 2-5% DMF, or in another embodiment about 2.5% DMF (relative to chloroform). In certain embodiments, completion of the reaction is monitored by treating an aliquot of the reaction mixture with methanol to form the methyl ester and the relative concentrations of ester and acid is determined by HPLC.

In some embodiments, after acid chloride formation to give a compound of formula (2a), the reaction mixture is reduced, in vacuo or by distillation (or both) to remove or at least minimise the amount of unreacted or excess chlorinating agent (for example, thionyl chloride).

Acid chloride (2a) is then dissolved in a polar aprotic solvent (for example, acetonitrile) and treated with a solution of lower alkyl N,N-lower dialkyl aminoacrylate and a non-nucleophilic organic base such as triethylamine (TEA), N,N-diisopropylethylamine (Hünigs base), or 1,8-diazabicycloundec-7-ene (DBU), to form a compound of formula (2b). In certain embodiments, the acrylate is ethyl N,N-dimethyl aminoacrylate (commercially available from Alfa Aesar) In certain embodiments, the solvent is acetonitrile. In other embodiments the acrylate is ethyl N,N-diethylamino acrylate or methyl N,N-diethylamino acrylate. Accordingly, in certain embodiments, both R' are ethyl. In other embodiments, both R' are methyl. In certain embodiments, a compound of formula (2a) is treated with about 2-6 molar equivalents of TEA and about 1.5-3.0 molar equivalents of ethyl N,N-dimethyl aminoacrylate. In other embodiments, a compound of formula (2a) is treated with about 4 molar equivalents of TEA and about 1.8 molar equivalents of ethyl N,N-dimethyl aminoacrylate.

In certain embodiments, the formation of a compound of formula (2b) by treating acid chloride (2a) with TEA and ethyl N,N-dimethyl amino acrylate is conducted at room temperature. In certain embodiments the reaction is conducted at a temperature range of 15-40° C., such as about 15° C., about 20° C., about 30° C., or about 40° C. In certain embodiments, the reaction is complete within about 2.5-3 hours. An aliquot can be quenched by MeOH for monitoring by HPLC.

In some embodiments, ring closure (or the cyclisation step) from a compound of formula (2b) to a compound of formula (3) occurs with the use of a lower alkyl amine as a solvent or within a solvent mixture in great excess relative to (2b). In certain embodiments, ring closure (i.e., cyclisation step) from (2b) to (3) occurs at refluxing temperatures. In an embodiment the reaction is conducted with acetonitrile under reflux. In certain embodiments the reaction is conducted at a temperature range of 50-100° C., such as about 50° C., about 60° C., about 70° C., about 80° C., about 90° C. or about 100° C. The progress of this reaction to form a compound of formula (3) may be followed by standard techniques such as thin layer chromatography (TLC), gas chromatography, LCMS monitoring, etc.

In some embodiments, the reaction step from (2b) to (3) is conducted by treating (2b) with an ethylamine solution. In certain embodiments, the ethylamine solution is an approximately 70 wt % ethylamine solution in water. In certain embodiments the cyclisation step the molar ratio of (2b) to lower alkyl amine is about 1:2.5. It will be appreciated that when this step is conducted with ethylamine this corresponds to Y being ethyl in the final product (i.e., compounds of formula (1)). In certain embodiments, the reaction mixture is cooled to about 25-30° C., added to a large excess of water at about 0-5° C., and kept at about 0-25° C. for 2-4 hours to give a solid. In certain embodiments, the solid is separated by filtration, washed with water, and dried.

Further optional purification of a compound of formula (3) may include column chromatography or recrystallization as the 1,8-naphthyridines of formula (3) are usually characterised as solids.

In certain embodiments, the 6-nitro group of a compound of formula (3) is subjected to reducing conditions to form a 6-amino analogue of formula (4). Suitable reducing agents include Fe and sodium dithionite. The reduction may also be facilitated by hydrogenation using palladium (Pd) or Raney nickel as catalysts.

In certain embodiments, the reducing step involves treating a compound of formula (3) with Fe and an aqueous acid (e.g., HCl or acetic acid) at a temperature of between 40°-60° C., for instance, about 50°-60° C.

In other embodiments, the reducing step involves treating a compound of formula (3) with sodium dithionite in an aqueous medium. In certain embodiments, the aqueous medium is an acetone/water mixture or acetone/HCl mixture. In certain embodiments, the reduction is conducted at elevated temperatures, for instance, about 50-70° C., or for instance, about 50-60° C.

In certain embodiments, the reduction of a compound of formula (3) occurs via hydrogenation over Pd or Ni based catalysts. In certain embodiments, the catalyst is a palladium catalyst (e.g., Pd/C). In other embodiments, the catalyst is Raney Ni. In certain embodiments, the reaction is conducted in a polar solvent, for instance, methanol or acidified methanol. In certain embodiment, the solvent also contains catalytic amounts of an acid such as acetic acid or hydrochloride acid. In certain embodiments, the reduction reaction is conducted at ambient temperature (room temperature), and with the use of hydrogen at atmospheric pressure or at a pressure between 1.8-2.4 $kg/cm^2$.

A list of exemplary reducing conditions includes:
  (i) Fe (3.0 eqs) and HCl (4.0 eqs) at 50° C.;
  (ii) Fe (3.0 eqs) and Acetic Acid (13-15 Vol) at 55-60° C.;
  (iii) Raney Ni, $H_2$, MeOH, or DCM+MeOH (1:1) or Aqueous MeOH or Ethyl acetate;
  (iv) Raney Ni, $H_2$, TFA or Acetic Acid (15%) in MeOH;
  (v) Sodium Dithionite (4.0 eqs) in 3:1 acetone:water or acetone:HCl (1N or 2N) at 55-60° C.;
  (vi) Pd over Carbon, $H_2$, (MeOH, or MeOH+1N HCl catalytic); and
  (vii) 10% Pd over Carbon (wet), $H_2$ (pressure 2 $kg/cm^2$), MeOH, 25-30° C.

In certain embodiments, the reducing step involves the hydrogenation of (3) to (4) with the use of Pd/C as a catalyst.

In certain embodiments, a compound of formula (4) is prepared with substantial purity such that no further purification is required prior to subjecting (4) to the next reaction step. Processing of (4) from the reaction medium in this regard simply entails separating (4) by phase separation techniques. The compound of formula (4) can also be subjected to further purification by column chromatography and/or recrystallisation, for instance, from ethanol.

In some embodiments, a compound of formula (4) is reacted with 2-indanone (commercially available from, for instance, Aldrich Chemicals) by reductive amination. The reductive amination reaction can occur in a single pot reaction using boron-containing reducing reagents, including, but not limited to, sodium borohydride, lithium borohydride, potassium borohydride, sodium triacetoxyborohydride, sodium cyanoborohydride, lithium triethylborohydride, pyridine borane, picoline borane, 5-ethyl-2-methylpyridine borane, tert-butylamine-borane in halogenated solvents such as dichloromethane or 1,2-dichloroethane, or alcohols such as methanol, ethanol or isopropanol, or polar aprotic solvents, such as dimethylsulfoxide, acetonitrile, or ethyl acetate, or ethers, such as tetrahydrofuran, dioxane, or 1,2-dimethoxyethane. In certain embodiments, a lower carboxylic acid such as acetic acid, propanoic acid, or butanoic acid is used as a co-solvent.

In certain embodiments, the reductive amination can also occur in two steps. Firstly by the formation of an imine in the presence of an acid including, but not limited to, lower carboxylic acids such as acetic acid, propanoic acid, butanoic acid, or p-toluenesulfonic acid or Amberlyst resin, and also a dehydrating reagent such as, but not limited to, magnesium sulphate, sodium sulphate, molecular sieves or $TiCl_4$, using, for example, dichloromethane, ethanol, ethyl acetate, tetrahydrofuran, 1,2-dimethoxyethane, or dimethyl sulfoxide as solvent. In certain embodiments, the imine formation step is performed in a Dean Stark apparatus using toluene at 90-110° C. In the second step, the imine can be converted to the secondary amine using the boron containing reducing agents as described above.

In certain embodiments, the reductive amination is conducted in a mixture of solvents comprising a halogenated solvent, ethers or alcohols with acetic acid.

In some embodiments, the reaction is conducted with the use of about 1-2.5 molar equivalents of 2-indanone relative to (4). In certain embodiments, about 1-1.6 molar equivalents of the borohydride or borane complex relative to (4) are employed. In certain embodiments, the reaction is conducted in a solvent system comprising a lower carboxylic acid such as acetic acid, propanoic acid, or butanoic acid and a solvent, such as ethanol, methanol, THF, dichloromethane (DCM) or 1,2-dichloroethane (DCE). In certain embodiments the lower carboxylic acid is acetic acid (AcOH). In certain embodiments, the ratio of AcOH:DCE is about 1:1 and the concentration of (4) is about 0.04-0.05 M. In certain embodiments, the reaction is conducted at temperatures below 40° C. under an inert atmosphere (e.g., nitrogen or argon). In other embodiments, the ratio of AcOH:EtOH is about 4:3 and the concentration of (4) is about 0.1-0.2 M. In other embodiments, the ratio of AcOH:THF is about 5:2, and the concentration of (4) is about 0.05-0.15 M.

In certain embodiments, a compound of formula (4) and 2-indanone are added to a AcOH:DCE (1:1) solvent system under an inert atmosphere. In certain embodiments, the reducing agent (e.g., borohydride) is added in a single portion. The reaction progress can be monitored by TLC.

In certain embodiments, a compound of formula (4) and 2-indanone are added to AcOH:EtOH (4:3) solvent system under an inert atmosphere. In certain embodiments, the reducing agent (e.g., 2-methylpyridine borane complex) is added as a single portion. The reaction progress can be monitored by LCMS.

If required, an additional amount of 2-indanone and reducing agent may be added in order to ensure that the reaction reaches completion.

Once completed, the reaction may be quenched (e.g., with a sodium hydrogen carbonate solution) and extracted with an organic solvent such as, for example, a chlorinated solvent (e.g., DCM) or ether. The resultant product (5) is ordinarily characterised as a solid and further purified (if required) by recrystallization and chromatography.

Accordingly, in a further aspect the invention provides a method of preparing a compound of formula (5)

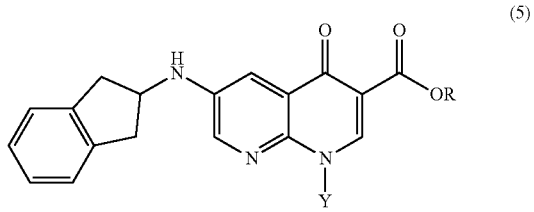

(5)

wherein R and Y are independently lower alkyl, comprising:
a) treating a compound of formula (4)

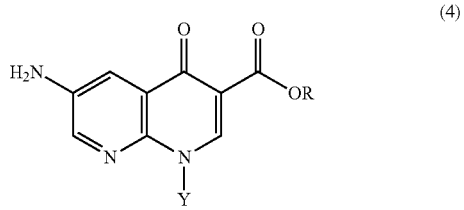

(4)

with 2-indanone and a suitable reducing agent under conditions sufficient to obtain a compound of formula (5),
wherein the reducing agent is 2-methylpyridine borane complex.

Hydrolysis of a compound of formula (5) to give a compound of formula (6) may be achieved by any conventional process. In some embodiments, the hydrolysis step is conducted under basic conditions (using, for instance, sodium hydroxide) in a polar solvent system (e.g., methanol or ethanol). In certain embodiments, the hydrolysis is conducted by dissolving a compound of formula (5) in an aqueous NaOH/ethanol solvent system. In certain embodiments, the hydrolysis is conducted at a temperature ranging from about room temperature to about 100° C. (for instance, from about 50 to 90° C.). The hydrolysis step can be monitored using TLC, and once completed the basic solvent system may be neutralised by the addition of a suitable acid (e.g. citric acid).

The product acid (i.e. a compound of formula (6)) is typically insoluble once the solvent system is neutralised and accordingly can be separated from the reaction mixture by simple filtration. Further purification, if required, can be achieved by recrystallization or other techniques known in the art. In other embodiments, the compound of formula (6) can be directly subjected to the next process step.

In another aspect, a method of the present invention comprises reacting a compound of formula (6) in situ with an acid activating agent and a nucleophilic QH group to prepare a 1,8-naphthyridine compound of formula (1) (wherein Q is an optionally substituted N-containing heterocycle or optionally substituted N-containing heteroaryl).

Suitable activating agents include pivaloyl chloride, lower alkyl chloroformates, carbonyl diimidazole (CDI), N,N'-dicyclohexylcarbodiimide (DCC), diisopropylcarbodiimide (DIC), 1-ethyl-3-(3-dimethylaminopropyl)carbodiimide (EDCI), benzotriazole-1-yl-oxy-tris-(dimethylamino)-phosphonium hexafluorophosphate (BOP), benzotriazol-1-yl-oxytripyrrolidinophosphonium hexafluorophosphate (PyBOP), hydroxybenzotriazole (HOBt), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), and propane phosphonic acid anhydride (T3P).

In certain embodiments, the activating agent is an alkyl chloroformate, such as ethyl chloroformate, n-propyl chloroformate, isopropyl chloroformate, tert-butyl chloroformate, or an acid chloride, such as pivaloyl chloride.

In certain embodiments, the reaction is conducted in the presence of a non-nucleophilic base such as TEA, Hünigs base, or 4-dimethylaminopyridine (DMAP) in a polar solvent, including, but not limited to, DCM, DCE, THF, or $CH_3CN$.

In other embodiments, a compound of formula (6) is converted to an acid chloride using suitable conditions before reaction with a nucleophilic QH group to prepare a 1,8-naphthyridine compound of formula (1) (wherein Q is an optionally substituted N-containing heterocycle or optionally substituted N-containing heteroaryl). It has been found, however, that in such a process care needs to be taken to ensure that any chlorination step does not chlorinate at the 4-oxo-position which may lead to undesirable by-products and reduced yields.

In certain embodiments, QH is morpholine.

Suitable conditions for the formation of an acid chloride include treatment of a solution of a compound of formula (6) in dichloromethane with 1-2 molar equivalents of thionyl chloride, or oxalyl chloride at 0-20° C. In certain embodiments, the reaction is performed in the presence of dimethylformamide (5-10% relative to dichloromethane).

In certain embodiments, the reaction is performed by treating a compound of formula (6) with an activating agent at a below ambient temperature (e.g., ~0-15° C.) and then adding the QH (preferably at about 1-1.2 molar equivalents relative to the compound of formula (6)) and allowing the reaction mixture to warm to room temperature or slightly higher, for instance, 50° C. The reaction progress can be monitored by TLC.

The present inventors have also discovered that a compound of formula (1) can be recovered in high purity from the final reaction step by washing the reaction mixture with a weakly basic solution (for instance, an aqueous $NaHCO_3$ solution) which removes much of the unreacted acid (6).

Further purification of (1), if required, may be conducted by standard techniques.

In certain embodiments, methods described herein allow for an overall yield of at least 15%, at least 20%, at least 25%, at least 30%, at least 40%, at least 50%, at least 60%, or at least 70% when performed on a gram scale or larger. In certain embodiments, methods described herein allow for an overall yield of at least 15%, at least 20%, at least 25%, at least 30%, at least 40%, at least 50%, at least 60%, or at least 70% when performed on a ten gram scale or larger. In certain embodiments, methods described herein allow for an overall yield of at least 15%, at least 20%, at least 25%, at least 30%, at least 40%, at least 50%, at least 60%, or at least 70% when performed on a hundred gram scale or larger. In certain embodiments, methods described herein allow for an overall yield of at least 15%, at least 20%, at least 25%, at least 30%, at least 40%, at least 50%, at least 60%, or at least 70% when performed on a five hundred gram scale or larger. In certain embodiments, methods described herein allow for an overall yield of at least 15%, at least 20%, at least 25%, at least 30%, at least 40%, at least 50%, at least 60%, or at least 70% when performed on a kilo gram scale or larger. In certain embodiments, methods described herein allow for an overall yield of at least 15%, at least 20%, at least 25%, at least 30%, at least 40%, at least 50%, at least 60%, or at least 70% when performed on a hundred kilogram scale or larger.

In relation to any one of the aforementioned scales the reductive amination step allows for a yield of isolated product of from about 60-80%, for instance, about 60%, about 65%, about 70%, about 75%, or about 80%. In certain embodiments the reductive amination step allows for an isolated yield of about 65%-80%.

In certain embodiments, the methods of the present invention are performed on a multi-gram scale. In certain embodiments, the methods of the present invention are performed on a kilogram scale. In certain embodiments, the methods of the present invention are performed on a multi-kilogram scale. In certain embodiments, the methods of the present invention are performed on an industrial scale (e.g., greater than hundreds of kilograms).

The following examples are intended to illustrate the invention and are not to be construed as being limitations thereon.

EXAMPLES

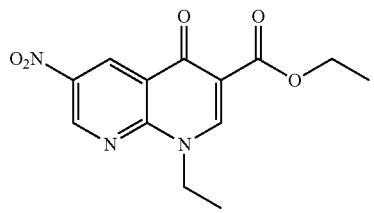 [SMILES: CCOC(=O)c1cn(CC)c2ncc([N+](=O)[O-])cc2c1=O]

vents were distilled under vacuum below 45° C. The residue was cooled to 25-30° C., and acetonitrile (10.0 L) was added at 25-30° C. with stirring.

Step 2: Triethylamine (10.0 kg), ethyl-3-(N,N-dimethylamino)acrylate and acetonitrile (12.5 L) were added to a glass flask at 25-30° C. The acid chloride solution prepared at step 1 was added to the reaction flask at 25-30° C. and the mixture was stirred for 2.5 h. The reaction mixture was monitored by quenching 0.5 mL of reaction mixture with 0.5 mL of methanol and recording the HPLC for methyl ester of 2-chloro-5-nitronicotinic acid (should be not more than 5.0%). After completion of the reaction (~4 h), 4.0 L of aqueous ethylamine solution (70%) was added slowly (~2.5 h), maintaining the reaction temperature at 25-30° C. The reaction mixture was heated to reflux for 2.5 h and monitored by HPLC for intermediate acrylate ester content (should be not more than 2.0%). The reaction was found to be complete by 8 h, and the reaction mixture was then cooled to 25-30° C. and maintained at this temperature for 3 h.

Step 3: 300.0 L of water was cooled to 0-5° C. in glass-lined reactor, and the reaction mixture from Step 2 was poured into it, maintaining the reactor temperature below 5° C. The reaction mixture was kept at 0-5° C. for ~3 h and the solid separated was filtered through Nutsche filter. The solvents were removed by filtration under vacuum. The wet cake was suspended in diethyl ether (25.0 L), mixed thoroughly and filtered through a Nutsche filter. The solvent was removed by filtration under vacuum and then material was loaded into drying trays. The solid was dried at 50-55° C. with hot air dryers until the water content was below 2.0% and then cooled to 25-30° C. to yield 68% of desired ester as a solid. $^1$H NMR (DMSO-d6, 500 MHz): 1.31(3H, t, J=7.0 Hz), 1.40 (3H, t, J=7.0 Hz), 4.27(2H, q, J=7.0 Hz), 4.54(2H, q, J=7.0 Hz), 8.96(1H, s), 9.07(1H, d, J=2.5 Hz), 9.59(1H, d, J=2.5 Hz). $^{13}$C NMR (DMSO-d6, 125 MHz): 14.16, 14.53, 46.63, 60.27, 113.00, 121.54, 131.45, 140.97, 147.70, 150.61, 151.22, 163.49, 172.57.

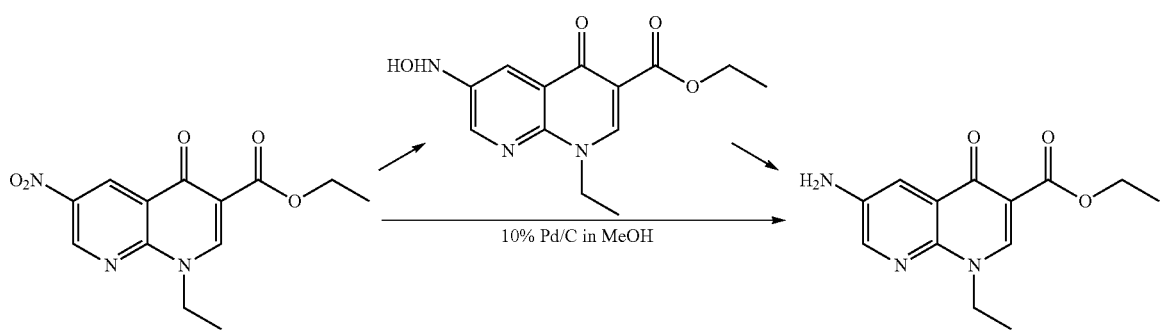

Ethyl 1-ethyl-6-nitro-4-oxo-1,8-naphthyridine-3-carboxylate

Ethyl 6-amino-1-ethyl-4-oxo-1,8-naphthyridine-3-carboxylate

Step 1: 2-Chloro-5-nitronicotinic acid (5.0 kg) was added to chloroform (20.0 L) at 25-30° C. under a nitrogen atmosphere. N,N-dimethylformamide (500 g) and thionyl chloride (6.0 kg) was sequentially added to the flask at 25-30° C. under a nitrogen atmosphere and the reaction mixture was heated to reflux. The reaction was monitored by quenching 1.0 mL of the reaction mixture with 10.0 mL of methanol and recording the HPLC for 2-chloro-5-nitronicotinic acid (should be not more than 10%). After completion of the reaction (~3 h), the reaction mass was cooled to 40-45° C., and the organic sol- The reactor was flushed with nitrogen gas continuously for 2-3 minutes. Methanol (255.0 L) was added to the reactor at 25-30° C. under nitrogen atmosphere. 306 g of palladium on carbon (10.0%) and ethyl 1-ethyl-6-nitro-4-oxo-1,8-naphthyridine-3-carboxylate (5.1 kg) was added to reactor sequentially under nitrogen atmosphere at 25-30° C. The reactor pressure was increased to 1.0 kg/cm$^2$ with nitrogen and then released slowly. This process was repeated three times. The reactor was filled with hydrogen gas and pressure was increased to 1.0 kg/cm$^2$ and then slowly released. This process was repeated three times and finally the hydrogen gas pressure was increased to 2.0 kg/cm$^2$ at 25-30° C. and maintained thereafter for 60-72 hrs.

The reaction progress was monitored by HPLC for consumption of starting material (should be no more than 2.0%) and intermediate hydroxylamine (should be no more than 10.0%). If the reaction progress was too slow, the hydrogen pressure was released slowly and additional 10% palladium over carbon (50 g) and methanol (50.0 L) were added and hydrogen pressure (2.0 kg/cm$^2$) was re-established. After completion of the reaction (64-75 h), the hydrogen pressure was released slowly and reactor was filled with nitrogen gas up to 1.0 kg/cm$^2$. The nitrogen pressure was released slowly and dichloromethane (128.0 L) was added.

A Hyflow bed was prepared in Nutsche filter with 2.60 kg of Hyflow and 29.1 L of dichloromethane. The filtrate was discarded. The reaction mixture was then filtered through the Hyflow bed under vacuum. The Hyflow bed was washed with a mixture of methanol (38.3 L) and dichloromethane (38.3 L). The filter was again subjected to vacuum. Filtrate was transferred into distillation flask and solvents were evaporated under vacuum below 50° C. The flask was cooled to 25-30° C. and acetone was added (25.5 L) at 25-30° C. The reaction mixture was stirred at 25-30° C. and then filtered through Nutsche filter under vacuum. The material was transferred to drying trays uniformly and dried with hot-air dryers at 40-45° C. dryers until the water content was below 0.5% and then cooled to 25-30° C. to yield 65% of desired compound as a solid. $^1$H NMR (DMSO-d6, 500 MHz): 1.29(3H, t, J=8.4 Hz), 1.35(3H, t, J=7.0 Hz), 4.23(2H, q, J=7.0 Hz), 4.43(2H, q, J=7.0 Hz), 5.80(2H, s), 7.67(1H, s), 8.26(1H, d, J=2.0 Hz), 8.67 (1H, s). $^{13}$C NMR (DMSO-d6, 125 MHz): 14.32, 15.08, 45.81, 59.51, 108.77, 115.12, 123.87, 140.08, 140.67, 143.57, 146.82, 164.69, 173.30.

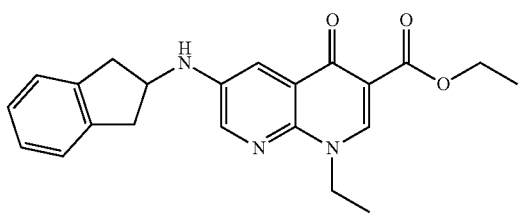 [SMILES: CCOC(=O)c1cn(CC)c2ncc(NC3Cc4ccccc4C3)cc2c1=O]

Ethyl 1-ethyl-6-(indan-2-ylamino)-4-oxo-1,8-naphthyridine-3-carboxylate

Step 1: 18.0 L of 1,2-dichloroethane (water content no more than 0.1%) and sodium borohydride (785 g) were sequentially added to a flask at 25-30° C. under nitrogen atmosphere. The reaction solution was cooled to 0-5° C. and 4.30 L of acetic acid (water content no more than 0.1%) was slowly added to reaction flask maintaining the temperature at 0-10° C. The reaction mixture was warmed to 25-30° C. and maintained at this temperature for 12 h.

Step 2: 1,2-dichloroethane (118.8 L), sodium sulphate (19.3 kg) and ethyl 6-amino-1-ethyl-4-oxo-1,8-naphthyridine-3-carboxylate (3.6 kg) were added sequentially to the reactor at 25-30° C. under a nitrogen atmosphere and cooled to 0-5° C. 2-Indanone (1.80 kg) was added to reaction mixture under stirring at 0-5° C., followed by slow addition of acetic acid (136.8 L) keeping temperature at 0-5° C. The reaction mixture was stirred at 0-5° C. for 10-15 minutes. 13.8 L of sodium triacetoxy borohydride solution (prepared at step 1) was added slowly in three installments of 4.6 L each at 0-5° C. and stirred at 0-5° C. for 2 h. Then, sodium sulphate (10.1 kg) and 2-indanone (878 g) were sequentially added to reaction mixture at 0-5° C. 8.0 L of the sodium triacetoxy borohydride solution (prepared at step 1) were slowly added to the reaction mixture at 0-5° C. and the reaction mixture was maintained at 0-5° C. for 10-12 h. The reaction progress was monitored by TLC for disappearance of starting material. After the completion of reaction (15 h), solvents were removed under vacuum below 60° C. and the reaction mass was cooled to 25-30° C. Dichloromethane (72.0 L) was added to reaction mixture with stirring at 25-30° C. and stirring was continued for 20-30 minutes. Then, reaction mixture pH was adjusted to 7-8 with aqueous sodium bicarbonate solution (prepared by dissolving 36 kg of sodium bicarbonate in 324 L of water) and the reaction mixture was stirred at 25-30° C. for 10-15 minutes. Two layers were allowed to separate over 15-20 minutes and then the organic layer was separated. Aqueous layer was washed with 36 L of dichloromethane twice and all organic layers were pooled, washed twice with water (2×36 L) and with aqueous sodium chloride solution (prepared by dissolving 7.2 kg of sodium chloride in 28.8 L of water); and finally dried over anhydrous sodium sulphate (1.8 kg) at 25-30° C. by stirring for 15-20 minutes. The solution was filtered through a Nutsche filter. The filtrate was transferred to a reactor and solvents were distilled under vacuum below 40° C.

Silica gel (25.2 kg) was added to plugged column and the crude reaction mass was loaded on column. The column was eluted with dichloromethane (1728.0 L), 5% ethyl acetate in dichloromethane (864 L), 7.5% ethyl acetate in dichloromethane (865 L) and 10% ethyl acetate in dichloromethane (1500 L). The fractions was analysed by TLC and the fractions containing pure material were pooled together in a reactor. The solvent was distilled out under vacuum below 45° C. and the remaining mass was cooled to 25-30° C. Diethyl ether (14.4 L) was added to reactor at 25-30° C. and stirred for 2.0 h. The reaction mass was filtered through Nutsche filter. The solid was spread over drying trays and dried with hot-air dryer at 35-40° C. yielding 2.2 kg of desired product as solid. $^1$H NMR (DMSO-d6, 500 MHz): 1.29(3H, t, J=7.0 Hz), 1.36 (3H, t, J=7.0 Hz), 2.84-2.88(2H, m), 3.5-3.39(2H, m), 4.22 (2H, q, J=7.0 Hz), 4.31-4.33(1H, m), 4.44(2H, q, J=7.0 Hz), 6.73(1H, d, J=6.5 Hz), 7.16-7.17(2H, m), 7.25-7.27(2H, m), 7.59(1H, d, J=3.0 Hz), 8.35(1H, d, J=3.0 Hz), 8.68(1H, s). $^{13}$C NMR (DMSO-d6, 125 MHz): 14.29, 15.10, 45.85, 53.07, 59.52, 109.00, 112.15, 123.78, 124.60, 126.36, 140.04, 140.69, 141.21, 142.78, 146.65, 164.72, 173.17.

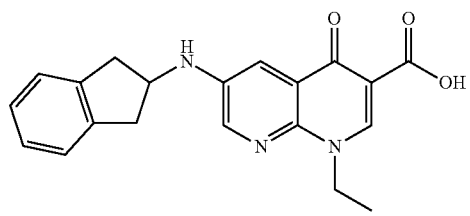 [SMILES: CCn1cc(C(=O)O)c(=O)c2cc(NC3Cc4ccccc4C3)cnc21]

1-Ethyl-6-(indan-2-ylamino)-4-oxo-1,8-naphthyridine-3-carboxylic Acid

Ethanol (42.0 L) was added to reactor at 25-30° C., followed by ethyl 1-ethyl-6-(indan-2-ylamino)-4-oxo-1,8-naphthyridine-3-carboxylate (4.20 kg) with stirring. Aqueous sodium hydroxide solution (prepared by dissolving 3.4 kg of sodium hydroxide into 42.0 L of water) was added to reaction mixture at 25-30° C. and reactor temperature was raised to 50-55° C. The reaction mixture was stirred at 50-55° C. for 2 h and reaction progress was monitored by TLC. After completion of hydrolysis (~3 h), the reaction mass was, cooled to 25-30° C. and pH was adjusted to 5-6 by addition of citric acid solution (prepared by dissolving 5.2 kg of citric acid in 47.0 L of water). The reaction mass was stirred for 20-25 minutes at 25-30° C. and filtered, the solid mass was washed with water (42.0 L) and acetone (21.0 L). The material was transferred to drying trays and dried with hot-air dryer at 70-75° C. until the water content decreased to 1.0%, yielding the desired compound (90%) as a solid. $^1$H NMR (DMSO-d6, 500 MHz): 1.40(3H, t, J=7.0 Hz), 2.86-2.90(2H, m), 3.37-3.41(2H, m), 4.38(1H, d, J=5.5 Hz), 4.62 (2H, q, J=7.0 Hz), 7.06(1H, d, J=6.0 Hz), 7.17-7.18(2H, m), 7.26-7.27(2H, m), 7.60(1H, d, J=2.5 Hz), 8.52(1H, d, J=2.0 Hz), 9.00 (1H, s), 15.30(1H, s). $^{13}$C NMR (DMSO-d6, 125 MHz): 15.19, 46.92, 52.92, 107.12, 109.42, 121.58, 124.63, 126.41, 140.11, 141.12, 143.33, 143.43, 145.93, 166.12, 177.53.

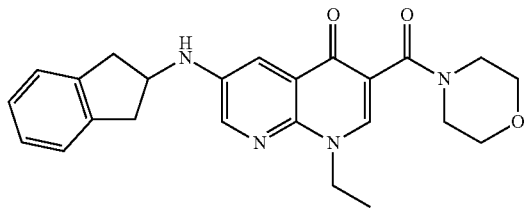 [SMILES: CCn1cc(C(=O)N2CCOCC2)c(=O)c2cc(NC3Cc4ccccc4C3)cnc21]

6-(2,3-Dihydro-1H-inden-2-ylamino)-1-ethyl-3-(morpholin-4-ylcarbonyl)-1,8-naphthyridin-4(1H)-one Step 1: 160.0 L of dichloromethane (water content should be no more than 0.1%), 1-ethyl-6-(indan-2-ylamino)-4-oxo-1,8-naphthyridine-3-carboxylic acid (4.0 kg) and triethylamine (3.5 kg) were sequentially added to reactor at 25-30° C. under nitrogen atmosphere and the reaction mixture was cooled to 10-15° C. Pivaloyl chloride (4.1 kg) was slowly added to reaction mixture keeping the reaction temperature at 10-15° C. Then, the reaction temperature was raised to 25-30° C. and stirred. The reaction progress was monitored by TLC for disappearance of starting material. After completion of reaction (3-4 h), the reaction mixture was again cooled to 15-20° C. and morpholine (6.0 kg) was added with stirring, keeping the reaction temperature at 15-20° C. N,N-Dimethyl-4-aminopyridine (194 g) and DMF (2.0 L) were added to the reaction mixture at 15-20° C. and heated to reflux. The reaction progress was monitored by TLC for the disappearance of intermediate pivaloyl ester and found to be complete within 12-13 h. The reaction mixture was cooled to 15-20° C. and then quenched by addition of aqueous sodium bicarbonate solution (prepared by dissolving 5.6 kg of sodium bicarbonate in 56.0 L of water) with stirring. The organic layer was separated and washed with aqueous sodium chloride solution (prepared by dissolving 23.0 kg of sodium chloride in 57.0 L of water). The organic layer was separated and dried by stirring with anhydrous sodium sulphate (4.0 kg). The organic layer was filtered through a Nutsche filter and the sodium sulphate was washed with dichloromethane. The filtrate was transferred into a flask and evaporated under vacuum below 40° C. The resulting material in the flask was cooled to 25-30° C. and suspended in diethyl ether (40.0 L). The solid separated was filtered using a Nutsche filter and washed with diethyl ether (8.0 L) and the isolated wet solid was dissolved in dichloromethane (20.0 L). The solution (10.0 L) was then filtered through a silica gel plug (10.0 kg) with dichloromethane (36.0 L), followed by 10 L of 10% methanol in dichloromethane. The silica gel filter was dried under vacuum. Similarly, the remaining portion of solution (10.0 L) was filtered through another silica gel plug (10.0 kg). The combined filtrate was evaporated under vacuum below 40° C. and then residual solid was suspended in ethyl acetate (20.0 L) with stirring at 25-30° C. The solid separated was filtered through Nutsche filter and washed with ethyl acetate (4.0 L). The filter was dried under vacuum and then material was transferred to drying trays and dried at 40-45° C. Yield (2.36 kg). $^1$H NMR (DMSO-d6, 500 MHz): 1.49 (3H, t, J=7.2 Hz), 2.91(2H, dd, J=3.5 Hz, 16.0 Hz), 3.42-3.47(4H, m), 3.80(6H, s), 4.25-4.26(1H, bd), 4.40-4.48(3H, m), 7.20-7.25(4H, m), 7.82(1H, d, J=3.0 Hz), 8.09 (1H, s), 8.18(1H, d, J=3.0 Hz). $^{13}$C NMR (CDCl$_3$, 150 MHz): 15.27, 39.87, 43.05, 46.66, 48.09, 53.93, 66.80, 67.40, 113.27, 116.71, 123.22, 124.92, 126.78, 140.87, 141.46, 141.83, 141.90, 143.84, 166.27, 173.38.

Alternative Methodologies for Preparing:

Ethyl 1-ethyl-6-(indan-2-ylamino)-4-oxo-1,8-naphthyridine-3-carboxylate

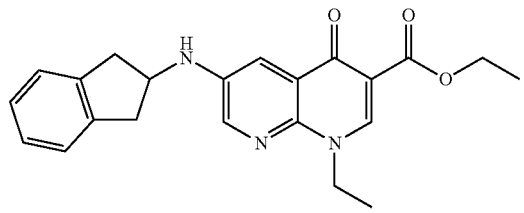 [SMILES: CCOC(=O)c1cn(CC)c2ncc(NC3Cc4ccccc4C3)cc2c1=O]

Method A. To a suspension of ethyl 6-amino-1-ethyl-4-oxo-1,8-naphthyridine-3-carboxylate (262 mg, 1.0 mmol) in anhydrous THF (3 mL) was added acetic acid (6 mL), and the mixture was stirred until all solids went into solution (may need to warm up to 40-45° C.). 2-Indanone (210 mg, 1.6 mmol) was added to the reaction mixture and stirred until completion of imine formation (indicated by disappearance of starting material by LCMS) (~30 min to 1 h). 2-Picoline borane complex (140 mg, 1.3 mmol) was added to reaction mixture and stirred vigorously to completion of imine reduction (disappearance of imine by LCMS). The reaction mixture was transferred to a beaker, diluted with ethyl acetate (20 mL), added an ice-cooled aqueous sodium hydroxide solution (1.0 M) (~90 mL, enough to quench almost 90% of acetic acid) and then basified with solid sodium bicarbonate. The organic layer was separated, washed with brine, dried over MgSO$_4$ and evaporated under reduced pressure to dryness. The crude was dissolved in dichloromethane (20 mL) and hexane (~20 mL) was added dropwise to cloudiness. The solid separated was washed with 1/1 mixture of diethyl ether and hexane to yield the desired compound as yellow solid (yield: 70%, HPLC Purity: 95%).

Method B. Step 1: To a suspension of ethyl 6-amino-1-ethyl-4-oxo-1,8-naphthyridine-3-carboxylate (261 mg, 1 mmol) in 4 mL of 1,2-dimethoxyethane was added acetic acid (8 mL) and the mixture was stirred until all solids went into solution (may need to warm up to 40-45° C.). 2-Indanone (180 mg, 1.4 mmol) was added to reaction mixture and stirred for 1 h. The reaction mixture was diluted with anhydrous diethyl ether (10 mL), the solid separated was filtered, washed with cold diethyl ether and dried under vacuum to yield imine as dark yellow solid (275 mg, 74%).

Step 2: Imine (275 mg, 0.74 mmol) was suspended in MeOH (5 mL) and acetic acid (5 mL), sodium cyanoborohydride (95 mg, 1.5 mmol) was added, and the mixture was vigorously stirred for 1 h. The reaction mixture was transferred to a beaker, diluted with ethyl acetate (40 mL), an ice-cooled aqueous sodium hydroxide solution (35 mL, 2.0 M) was added (enough to quench almost 90% of acetic acid) and then the reaction mixture was further basified with solid sodium bicarbonate to pH 7-8. The organic layer was separated, washed with brine, dried over $MgSO_4$ and evaporated under reduced pressure to dryness to dark yellow solid (260 mg, 95%, HPLC purity: 87%).

Other Alternative Methods. To a suspension of ethyl 6-amino-1-ethyl-4-oxo-1,8-naphthyridine-3-carboxylate in a solvent specified in Table 1 was added acetic acid and the mixture was stirred until all solids went into solution (may need to warm up to 40-45° C.). 2-Indanone was added to reaction mixture and stirred to completion of imine formation (indicated by disappearance of starting material in LCMS) (~30 min to 1 h). Boron reducing agent (as listed in Table 1) was added to reaction mixture and stirred vigorously to completion of imine reduction (disappearance of imine in LCMS). The reaction mixture was transferred to a beaker, diluted with ethyl acetate, added an ice-cooled aqueous sodium hydroxide solution (1.0 M) (enough to quench almost 90% of acetic acid) and then further basified with solid sodium bicarbonate to pH 7-8. The organic layer was separated, washed with brine, dried over $MgSO_4$ and evaporated under reduced pressure to dryness. Where specified in Table 1, the crude was passed through a plug of silica gel with increasing gradient of EtOAc in DCM to offer the required product as dark yellow solid.

Alternative Methodologies for Preparing:

6-(2,3-Dihydro-1H-inden-2-ylamino)-1-ethyl-3-(morpholin-4-ylcarbonyl)-1,8-naphthyridin-4(1H)-one

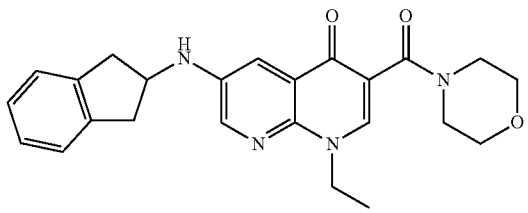 [SMILES: CCn1cc(C(=O)N2CCOCC2)c(=O)c2cc(NC3Cc4ccccc4C3)cnc21]

Method A. To a suspension of 1-ethyl-6-(indan-2-ylamino)-4-oxo-1,8-naphthyridine-3-carboxylic acid (350 mg, 1 mmol) in anhydrous DCM (16 mL) was added $NEt_3$ (280 μL, 2 mmol) and the reaction mixture was cooled to 0° C. in ice bath. Ethyl chloroformate (143 μL, 1.5 mmol) was added to reaction mixture via syringe and the reaction was stirred for 10 min. The ice bath was removed and the reaction temperature was allowed to rise to room temperature and stirred to completion of reaction (~20 min). The reaction mixture was again cooled in ice-bath and morpholine (261 mg, 3 mmol) was added via syringe. The reaction mixture stirred at room temperature until the amide formation was complete (~30 min). The reaction mixture was again cooled in ice-bath and quenched by addition of few drops of methanol, then diluted with ethyl acetate. The organic layer was washed with $NaHCO_3$ (sat. aq.), brine, separated, dried over $MgSO_4$ and evaporated to dryness. The crude was dissolved in MeOH (5 mL) and hot water (7 mL, at ~70° C.) was added to it. The solid separated was filtered and dried under high

TABLE 1

Conditions for the preparation of ethyl 1-ethyl-6-(indan-2-ylamino)-4-oxo-1,8-naphthyridine-3-carboxylate.

| | Amine | 2-Indanone (eq)/ Reducing Agent (eq) | Solvent Solvents (Ratio) | Total Volume | Reaction Time (h) | Yield % |
|---|---|---|---|---|---|---|
| 1. | 262 mg | 2.5 eq/ $Na(OAc)_3BH$ (2.5 eq) | THF/AcOH (2/5) | 14 mL | 2.5 h | 65** |
| 2. | 100 mg | 1.2 eq/ $Na(OAc)_3BH$ (2.5 eq) | THF/AcOH (1/2) | 4.5 mL | 2.5 h | 64* |
| 3. | 100 mg | 1.2 eqs/ $Na(OAc)_3BH$ (2.5 eq) | DCM/AcOH (1/2) | 4.5 mL | 2.5 h | 59* |
| 4. | 2.61 g | 1.3 eqs./ $NaCNBH_3$ (2.0 eqs.) | EtOH/AcOH (3/4) | 70 mL | 2.5 h | 74** |
| 5. | 261 mg | 1.5 eq/ $NaCNBH_3$ (1.2 eq) | 1,2-DME/AcOH (1/1) | 10 mL | 2.5 h | 78* |
| 6. | 261 mg# | 1.5 eq/ $NaCNBH_3$ (1.2 eq) | 1,2-DME/AcOH (1/1) | 10 mL | 2.5 h | 73* |
| 7. | 150 mg | 1.3 eq/ $NaCNBH_3$ (1.7 eq) | THF/AcOH (1/2) | 6 mL | 2.5 h | 57* |
| 8. | 150 mg | 1.7 eq/ $NaCNBH_3$ (1.2 eq) | EtOAc/MeOH/AcOH (1/1/3) | 5 mL | 2.0 h | 75* |
| 9. | 261 mg | 1.1 eqs/ $NaCNBH_3$ (1.7 eq) | MeOH/AcOH (2/3) | 5 mL | 1.0 h | 70* |

*Yield from LCMS-HPLC of crude.
**Isolated yield after column purification.
Anhydrous $MgSO_4$ (10 eq) was added to reaction mixture.

vacuum to yield the required material as pale yellow solid (350 mg, 84%, HPLC Purity: 99%).

Method B. To a suspension of 1-ethyl-6-(indan-2-ylamino)-4-oxo-1,8-naphthyridine-3-carboxylic acid (248 mg, 0.7 mmol) in 1/1 DCM/DMF (12 mL) was added morpholine (400 µL, 4.6 mmol), followed by HATU (305 mg, 0.8 mmol) in one portion. The reaction was warmed to 50° C. until the completion of reaction (~1 h). The reaction was quenched with NaHCO₃ (sat. aq.) and extracted with DCM. The extracts were combined, washed with H₂O and brine, dried over MgSO₄, filtered and concentrated in vacuo. The crude was passed through a small plug of silica gel with increasing gradient of MeOH (1% to 5%) in DCM to yield required as pale yellow solid (164 mg, 55%).

The invention claimed is:

1. A method of preparing a compound of formula (1)

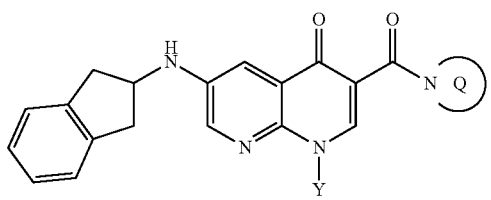
(1)

wherein Q is an optionally substituted N-containing heterocyclyl or optionally substituted N-containing heteroaryl, and Y is a lower alkyl group;

said method comprising:

a) treating a compound of formula (2)

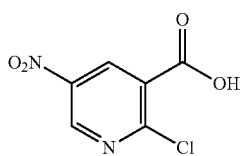
(2)

with an acid activating agent, a non-nucleophilic base, lower alkyl N,N-lower dialkyl aminoacrylate and lower alkylamine, under conditions sufficient to obtain a compound of formula (3)

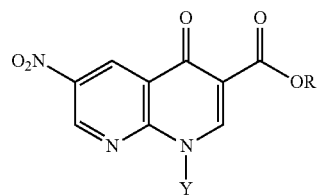
(3)

wherein R is lower alkyl, b) reducing the nitro group of the compound of formula (3) from step (a) to obtain a compound of formula (4)

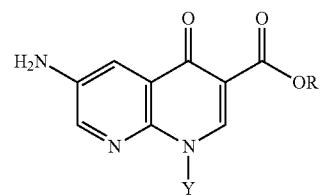
(4)

c) treating the compound of formula (4) from step (b) with 2-indanone and a suitable reducing agent under conditions sufficient to obtain a compound of formula (5)

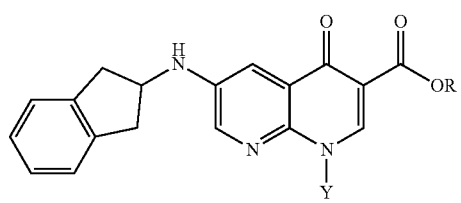
(5)

d) hydrolysing the compound of formula (5) from step (c) to obtain a compound of formula (6); and

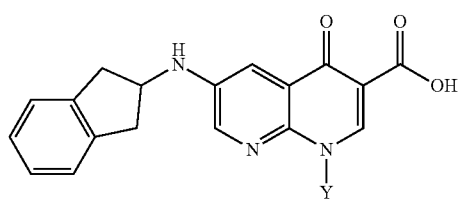
(6)

e) reacting (6) with an acid activating agent and QH, under conditions sufficient to obtain a compound of formula (1).

2. A method according to claim 1 wherein the acid activating agent in step a) is thionyl chloride, and the reaction takes place in a chlorinated solvent.

3. A method according to claim 2 wherein the reaction is conducted in the presence of a catalytic amount of DMF.

4. A method according to claim 1 wherein the non-nucleophilic base is triethylamine (TEA).

5. A method according to claim 1 wherein the lower alkyl-N,N-lower dialkyl aminoacrylate is ethyl N,N-dimethyl aminoacrylate.

6. A method according to claim 1 wherein the lower alkyl amine is ethylamine.

7. A method according to claim 1 wherein the step of reducing the nitro group involves subjecting a compound of formula (3) to a suitable reducing agent selected from Fe or sodium dithionite, or hydrogenation of a compound of formula (3) using palladium (Pd) or Raney nickel as catalysts.

8. A method according to claim 1 wherein the reducing agent in step (c) is a boron containing reducing agent selected from sodium borohydride, lithium borohydride, potassium borohydride, sodium triacetoxyborohydride, sodium cyanoborohydride, lithium-triethylborohydride, pyridine borane, picoline borane, 5-ethyl-2-methylpyridine borane, and tert-butylamine-borane.

9. A method according to claim 1 wherein step (c) is conducted in the presence of an organic solvent with a lower carboxylic acid used as a co-solvent.

10. A method according to claim 1 wherein step (c) is conducted as a two-step process with the initial formation of an imine.

11. A method according to claim 1 wherein the compound of formula (4) in step (b) is treated with about 1-2.5 molar equivalents of 2-indanone.

12. A method according to claim 1 wherein the acid activating agent in step e) is an alkyl chloroformate or an acid chloride.

13. A method according to claim 12 wherein reaction step (e) is conducted in the presence of TEA in a chlorinated solvent.

14. A method according to claim 1 wherein step (e) includes treatment of a solution of compound of formula (6) in dichloromethane with 1 to 2 molar equivalents of thionyl chloride or oxalyl chloride at a temperature of 0 to 20°C.

15. A method according to claim 14 wherein the solution includes DMF at a concentration of about 5 to 10% relative to the dichloromethane.

16. A method according to claim 1 wherein QH is morpholine.

17. A method according to claim 1, wherein step (a) comprises treating the
compound of formula (2)

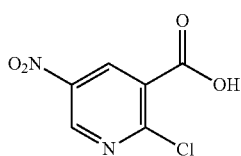
(2)

with an acid activating chlorinating agent under conditions sufficient to obtain a compound of formula (2a)

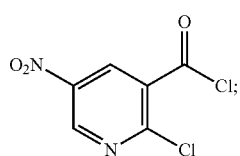
(2a)

treating the compound of formula (2a) with the non-nucleophilic base and the lower alkyl N,N-lower dialkyl aminoacrylate to obtain a compound of formula (2b)

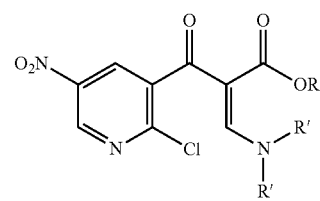
(2b)

wherein R and R' are independently lower alkyl; and reacting the compound of formula (2b) with the lower alkylamine under conditions sufficient to form the compound of formula (3)

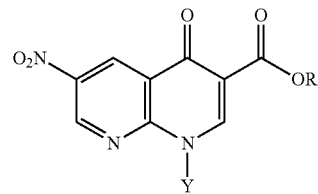
(3)

wherein Y and R are independently lower alkyl.

18. A method for preparing a compound of formula (1)

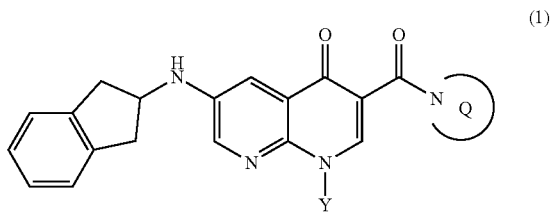
(1)

wherein Q is an optionally substituted N-containing heterocyclyl or optionally substituted N-containing heteroaryl and Y is a lower alkyl group;
said method comprising:
a) reacting a compound of formula (6)

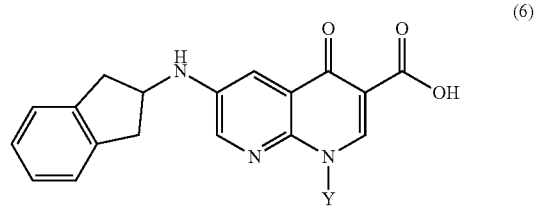
(6)

with an acid activating agent in the presence of non-nucleophilic base in a suitable solvent and reacting the resultant product with QH under conditions sufficient to obtain a compound of formula (1); and
b) purifying the compound of formula (1) obtained from step a) by washing with a weakly basic solution.

19. A method according to claim 1, wherein step (c) comprises
treating the compound of formula (4)

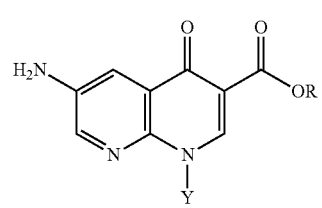
(4)

with 2-indanone and a suitable reducing agent under conditions sufficient to obtain the compound of formula (5), wherein the reducing agent is 2-methylpyridine borane complex.

* * * * *